United States Patent [19]

Ghisalba et al.

[11] Patent Number: 5,098,841
[45] Date of Patent: Mar. 24, 1992

[54] PROCESS FOR THE PREPARATION OF HYDROXY ACIDS

[75] Inventors: Oreste Ghisalba, Reinach; Daniel Gygax, Himmelried; Renté Lattmann, Binningen; Hans-Peter Schär, Aesch, all of Switzerland; Elke Schmidt, Freiburg; Gottfried Sedelmeier, Schallstadt, both of Fed. Rep. of Germany

[73] Assignee: CIBA-GEIGY Corporation, Ardsley, N.Y.

[21] Appl. No.: 360,802

[22] Filed: Jun. 2, 1989

[30] Foreign Application Priority Data

Jun. 6, 1988 [CH] Switzerland .............. 2138/88

[51] Int. Cl.$^5$ .............................. C12P 7/42
[52] U.S. Cl. .................... 435/280; 435/146
[58] Field of Search ................ 435/280, 146

[56] References Cited

U.S. PATENT DOCUMENTS

4,326,031  4/1982  Wandrey et al. ............ 435/146

FOREIGN PATENT DOCUMENTS

000560  2/1979  European Pat. Off. .

OTHER PUBLICATIONS

Dollar–Chem. Abst., vol. 70 (1969), p. 64543g.
Goetz et al., Chem. Abst. vol. 86 (1977), p. 67303v.
Simon et al., Angewandte Chemie, vol. 97, pp. 541–555 (1985).
Wipf et al., Helvetica Chim. Acta Vol. 66, pp. 485–487 (1983).
Günther et al., Jour. of Biotech., vol. 5, pp. 53–65 (1987).
Yamazaki et al., Agric. Biol. Chem., vol. 50, No. 10, pp. 2621–2631 (1986).
Yamazaki et al., Agricol. Biol. Chem., vol. 50, No. 12, pp. 3213–3214 (1986).

*Primary Examiner*—Sam Rosen
*Attorney, Agent, or Firm*—Irving M. Fishman; Karen G. Kaiser

[57] ABSTRACT

The invention relates to a preferably continuous process for the preparation of R- or S-2-hydroxy-4-phenylbutyric acid in very high enantiomeric purity, which comprises reducing 2-oxo-4-phenylbutyric acid with the enzyme D-lactate dehydrogenase from *Staphylococcus epidermidis* or with the enzyme L-lactate dehydrogenase from bovine heart, respectively, in the presence of NAD(H) and formate or ethanol and formate dehydrogenase or alcohol dehydrogenase, respectively. R-2-hydroxy-4-phenylbutyric acid is a valuable intermediate in the preparation of ACE inhibitors or their precursors.

10 Claims, No Drawings

PROCESS FOR THE PREPARATION OF HYDROXY ACIDS

The present invention relates to a process for the preparation of the R-enantiomer of 2-hydroxy-4-phenylbutyric acid of the formula

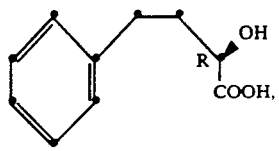

or the S-enantiomer of 2-hydroxy-4-phenylbutyric acid of the formula

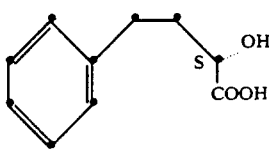

of very high enantiomeric purity, e.g. in the region of 99 % ee (enantiomeric excess), preferably of more than 99.6 % ee, which process comprises reducing 2-oxo-4-phenylbutyric acid with the enzyme D-lactate dehydrogenase (D-LDH) from *Staphylococcus epidermidis* or with the enzyme L-lactate dehydrogenase (L-LDH) from bovine heart, respectively, in the presence of an electron donor, for example NAD(H), and an enzyme/substrate system for regenerating the electron donor, for example formate dehydrogenase (FDH)/formate. The process for the preparation of R-2-hydroxy-4-phenylbutyric acid of formula I is preferably carried out with the enzyme D-LDH from *Staphylococcus epidermidis* in the presence of an electron donor, for example NAD(H), and an enzyme/substrate system for regenerating the electron donor, for example formate dehydrogenase (FDH)/formate. The process of the invention is especially suitable for continuous enzymatic conversion, preferably in an enzyme membrane reactor (EMR).

R-2-hydroxy-4-phenylbutyric acid of formula I is a valuable intermediate in the preparation of ACE (angiotensin converting enzyme) inhibitors or their precursors. S-2-hydroxy-4-phenylbutyric acid of formula II is used for the preparation of isomeric compounds.

The production of chiral compounds by stereospecific microbiological reduction is known (see Simon et al., Angew. Chemie 97. 541, 1985 for a summary). Frequently, intact microorganisms are used as biocatalysts, for example fungi (e.g. Mucor. Geotrichum, Saccharomyces, Candida) or bacteria (e.g. Proteus, Pseudomonas). It is also possible to use microbial extracts. Electron donors are, for example, carbohydrates (e.g. glucose), formate, ethanol, hydrogen or the cathode of an electrochemical cell. The reduction of the substrate is effected by the so-called final reductase, e.g. by a substrate-specific dehydrogenase. The reduction equivalents required by the final reductase are generally provided by a coenzyme, e.g. by pyridine nucleotides such as NADH (nicotinamide adenine dinucleotide) and NADPH (nicotinamide adenine dinucleotide phosphate) or by flavine nucleotides such as FMNH (flavine mononucleotide) and FADH (flavine adenine dinucleotide). The reduced nucleotides are in turn usually produced in a series of enzyme-catalysed steps in which competing electron acceptors are formed or by electron transfer by natural or synthetic mediators (e.g. ferredoxin, viologens). Also known are final reductases that are able to accept electrons directly from the mediators.

Also suitable as biocatalysts are purified enzymes, i.e. isolated reductases, in which case it is generally necessary to add reduced pyridine nucleotides or flavine nucleotides. A further requirement is an efficient system for enzymatic regeneration of the coenzyme, i.e. a second enzyme and its substrate. Yamazaki & Maeda (Agricol. Biol. Chem. 50. 2621, 1986) describe a batch process for the synthesis of R-(−)-mandelic acid from benzoyl formate with the aid of NADH and the benzoyl formate dehydrogenase from *Streptococcus faecalis*. This process can also be carried out continuously in a bioreactor with the coenzyme being regenerated by means of formate dehydrogenase and formate (Yamazaki & Maeda, Agricol. Biol. Chem. 50, 3213, 1986). European Patent Specification EP 0 024 547 describes a process for the continuous enzymatic conversion of water-soluble o-ketocarboxylic acids into the corresponding α-hydroxycarboxylic acids in an enzyme membrane reactor. The conversion is carried out in the presence of NAD(H) of which the molecular weight has been increased by bonding to polyethylene glycol and in the presence of a lactate dehydrogenase with simultaneous NADH regeneration by formate dehydrogenase and formate. Of crucial importance in enzymatic reactions are the properties and the origin of the enzyme used, that is to say in this case the final reductase or the substrate-specific dehydrogenase. It must be kept in mind that even enzymes of the same type may differ in their physiological behaviour if they have been isolated from different sources, for example different microorganisms. Differences exist with regard to such decisive parameters for the bioconversion as reaction specificity, substrate specificity and stereospecificity and kinetic factors such as the Michaelis-Menten constant and the inhibition constant (Simon et al., loc. cit.). For example, by comparing the data from the known literature it will be apparent that while D-lactate dehydrogenase from *Lactobacillus confusus* converts pyruvate, 2-ketobutyrate and phenylpyruvate, this enzyme does not reduce 2-ketovalerate, 2-ketocaproate and 2-keto-3-methylvalerate. The behaviour of individual enzyme/substrate systems must, therefore, be tested for each case and cannot be predicted by generalisation, although EP 0 024 547 points to that conclusion.

The object of the present invention is to find efficient processes for the preparation of the R- and S-enantiomers of 2-hydroxy-4-phenylbutyric acid with a high degree of enantiomeric purity by enantioselective enzymatic reduction of 2-oxo-4-phenylbutyric acid. This substance has not been described as a substrate in the prior art relating to enzymatic reduction of α-ketocarboxylic acids and, accordingly, has not been investigated with regard to its suitability and its behaviour in enzymatic reduction.

A process that has been found especially suitable for achieving that object with regard to the preparation of R-2-hydroxy-4-phenylbutyric acid is one in which the substrate is reduced with the enzyme D-lactate dehydrogenase from *Staphylococcus epidermidis* in the presence of an electron donor and an enzyme/substrate system for regenerating the electron donor, since, compared with lactate dehydrogenases from other microorganisms, the D-LDH from *Staphylococcus epidermidis* is distinguished especially by a high specific activity (units/mg converted substrate or μmol conversion/mg protein x min.) with regard to the substrate used (see Table 1) and has a high enantioselectivity. For the same reasons, an analogous process, in which the substrate is reduced with the enzyme L-lactate dehydrogenase from bovine heart, is especially suitable for the preparation of S-2-hydroxy-4-phenylbutyric acid. The continuous reaction method, especially in an enzyme membrane reactor, is preferred for both processes.

TABLE 1

Comparison of the specific activity of commercially available dehydrogenases

| enzyme source | | U/mg protein based on pyruvate | U/mg protein based on 2-keto-4-phenyl-butyric acid |
|---|---|---|---|
| D-LDH | *Lactobacillus leichmannii* Boehringer 732737 | 300 | ~0.1 |
| D-LDH | *Lactobacillus leichmannii* Sigma L 2011 | 300 | 0.3 |
| D-LDH | *Leuconostoc mensenteroides* Sigma L 0513 | 1000–1500 (1225) | 1.23 |
| D-LDH | *Staphylococcus epidermidis* Sigma L 9636 | 500–1000 (625) | 26 |
| L-LDH | bovine heart Fluka 61310 | 300 | 0.07 |

700 U = 1 mole product/day

The combination of D-LDH from *Staphylococcus epidermidis* as the substrate-specific dehydrogenase of high enantioselectivity and 2-oxo-4-phenylbutyric acid as the substrate offers the guarantee of high productivity figures, good space-time yields and, consequently, cheapness which is of great importance and considerable economic advantage in enzymatic conversions carried out on a large scale.

The electron donor used for the D-lactate dehydrogenase from *Staphylococcus epidermidis* or for the L-lactate dehydrogenase from bovine heart is preferably the coenzyme nicotinamide adenine dinucleotide in its reduced form (NADH) which is oxidised by the D- or L-LDH to NAD. For the regeneration of the coenzyme, an enzyme/substrate system consisting of a NADH-recycling enzyme and its substrate, e.g. formate, ethanol, isopropanol, cyclohexanol etc., is used. A formate dehydrogenase (FDH)/ formate system in which a salt of formic acid, for example an alkali metal formate, e.g. potassium or sodium formate, is used as the formate or an alcohol dehydrogenase (ADH)/ethanol system is preferred. These systems produce $CO_2/HCO_3^-$ and acetaldehyde, respectively, as by-products.

The process of the invention yields the product R- or S-2-hydroxy-4-phenylbutyric acid with a high degree of enantiomeric purity. In the context of this description, the expression "with a high degree of enantiomeric purity" means that the enantiomer in question is present with at least 98% ee in the mixture with the other enantiomer, preferably with more than 99% ee.

In the batch process, an aqueous solution of the substrate 2-oxo-4-phenylbutyric acid, for example in the form of its potassium or sodium salt, in a concentration of up to 500 mM, for example in a concentration of from 20 to 200 mM, preferably of 50 mM, is incubated while stirring with the coenzyme NAD(H) in a concentration of from 0.01 to 10 mM, preferably of approximately 0.1 mM, the NADH-recycling enzyme, e.g. an alcohol dehydrogenase or a formate dehydrogenase, and ethanol or formate, respectively, in a concentration of from 100 to 1200 mM, preferably of approximately 300 mM, and with the D-lactate dehydrogenase from *Staphylococcus epidermidis* or with the L-lactate dehydrogenase from bovine heart until conversion is complete. The enzymes are advantageously used in such quantities that the ratio of the activities of NADH-recycling enzyme and substrate-specific dehydrogenase is from 1:0.1 to 1:5. The reaction mixture has a pH in the range of from pH 6 to 9, e.g. pH 8.4, as is customary for enzymatic reactions. The reaction temperature is from 20° C. to 40° C., preferably around room temperature. The product is crystallised from the reaction mixture by the addition of an acid, for example a mineral acid, such as hydrochloric acid etc..

For the continuous reaction method the enzymes used are generally immobilised. They may be, for example, enclosed in polymer matrices, in capsules or fibres consisting of semipermeable membranes or by ultra-filtration membranes, or crosslinked with bifunctional or multifunctional reagents, or fixed by adsorption or by ionic or covalent bonding to carriers consisting of inorganic material or of natural or synthetic polymers. Numerous types of bioreactor can be used for the continuous process, e.g. stirred reactors, fixed bed reactors, fluidised bed reactors or membrane reactors (see Hartmeier, "Immobilisierte Biokatalysatoren", Berlin 1986 for a summary).

In the EMR process (continuous process in an enzyme membrane reactor) of the invention, the reaction vessel used is preferably a membrane reactor equipped with an ultrafiltration membrane that retains the enzymes used and the coenzyme required for the conversion but allows the low molecular weight product and the unconverted substrate to pass through. A considerable advantage of membrane reactors is that the biocatalysts can be used in native form, i.e. in unmodified form, and do not have to be subjected to any of the fixing steps otherwise required for immobilisation which usually have an inactivating effect. The enzyme membrane reactor may be, for example, a flat membrane (chamber membrane) reactor or a hollow fibre membrane reactor. The substrate is fed to the reaction chamber, for example, by a metering pump, the reaction mixture is stirred or pumped round and the stream of filtrate passing through the membrane, which contains the product, is drawn off. The membranes used for the process of the invention are preferably those having a nominal exclusion limit of from 5,000 to 100,000 daltons, e.g. from 10,000 to 100,000 daltons. Suitable materials for the membranes are, for example, acetylcelluloses, polyamides, polysulfones or modified polyvinyl alcohols. In order to prevent the enzymes involved in the reaction from being adsorbed on the membrane, the membrane can be pre-coated with a non-specific protein, for example bovine serum albumin.

The reaction mixture in the membrane reactor contains the NADH-recycling enzyme, for example an alcohol dehydrogenase or, preferably, a formate dehydrogenase, the D-lactate dehydrogenase from *Staphylococcus epidermidis* or the L-lactate dehydrogenase from bovine heart, and NAD(H). The NADH-recycling enzyme is advantageously used in such a quantity that the ratio of the activities of NADH-recycling enzyme and substrate-specific dehydrogenase is from 1:0.1 to 1:5. The coenzyme required is used in the form of NAD(H) of which the molecular weight has not been increased, i.e. native NAD(H), in a concentration of from 0.01 to 10 mM, preferably of about 0.1 mM. The possibility of also using native NAD(H) in an enzyme membrane reactor in the process of the invention has distinct advantages over the prior art described in EP 0 024 547. EP 0 024 547 specifies the use of NAD(H) that has been bonded to a polyethylene glycol in order to increase the molecular weight. This bonding, however, may result in a loss of the enzymes' activity. For example, when PEG-NAD(H) is used as the coenzyme, as opposed to native NAD(H), the activity of the D-lactate dehydrogenase from *Staphylococcus epidermidis* is so severely restricted that the $V_{max}$ value, that is the maximum reaction rate, is only 2.6 units/mg as compared with 26 units/mg for native NAD(H). If adequate conversion rates of the substrate are to be achieved in a continuous process using PEG-NAD(H), it is therefore necessary to use approximately ten times as much enzyme in the EMR, which results in a sharp increase in production costs. In order to retain efficiently behind an ultrafiltration membrane, for example, NAD(H) of which the molecular weight has been increased by bonding to a polyethylene glycol of molecular weight 20,000, the membrane may have a maximum exclusion limit of 10,000 daltons. On the other hand, when catalytic amounts of native NAD(H) are used in the substrate stream, the exclusion limit of the membrane is determined only by the size of the enzyme. It is therefore possible to use membranes having exclusion limits of from 5,000 to 100,000 daltons, so that high pressure in the reactor, which limits the running time of the reactor, can be avoided. Owing to the low pressure when using native NAD(H) it is also possible to use smaller and, therefore, less expensive membranes and to achieve higher throughput rates. When using native NAD(H), high cycle figures in the range of from 500 to 2,000 also are achieved, that is to say, per molecule of NAD(H), from 500 to 2,000 molecules of hydroxy acid are formed. The process of the invention thus offers considerable economic advantages over the process described in EP 0 024 547.

In addition, an aqueous solution of 2-oxo-4-phenylbutyric acid, for example in the form of its potassium or sodium salt, is fed continuously to the reactor as the substrate. The substrate should be present in a concentration of not more than 500 mM; a concentration in the range of from 20 to 200 mM, especially of about 50 mM, is preferred. Formate or ethanol are also metered in continuously in a concentration of from 100 to 1200 mM, preferably in a concentration of about 300 mM for formate.

The reaction mixture has a pH in the range of from pH 6 to 9, e.g. around pH 8.4, as is customary for enzymatic reactions. The reaction temperature is from 20° to 40° C., preferably around room temperature.

A preferred process of the invention is one as described above wherein the enzymatic conversion is carried out in an enzyme membrane reactor a) that is equipped with an ultrafiltration membrane having a nominal exclusion limit of, for example, from 5,000 to 100,000 daltons, preferably from 10,000 to 100,000 daltons, which has optionally been pre-coated with a non-specific protein, e.g. bovine serum albumin, b) that contains a reaction mixture consisting of a solution of a formate dehydrogenase or an alcohol dehydrogenase, preferably a formate dehydrogenase, the D-lactate dehydrogenase from *Staphylococcus epidermidis* or the L-lactate dehydrogenase from bovine heart, and nicotinamide adenine dinucleotide (NAD(H)) in a concentration of, for example, from 0.01 to 1 mM, preferably of about 1 mM, c) to which there is continuously fed an aqueous solution of the substrate 2-oxo-4-phenylbutyric acid, for example in the form of its potassium or sodium salt, in a concentration of up to 500 mM, for example in a concentration of from 20 to 200 mM, preferably of about 50 mM, and formate, for example potassium or sodium formate, or, respectively, ethanol, for example in a concentration of from 100 to 1200 mM, preferably of about 300 mM, and d) in which the compound formed is continuously drawn off downstream of the membrane.

R-2-hydroxy-4-phenylbutyric acid is a valuable intermediate in the preparation of ACE inhibitors or their precursors. This class of active substances has been the subject of growing interest in recent years. It broadens the potential of the available antihypertensives and therewith the possible therapies for the control of high blood pressure. A significant structural element in a number of effective ACE inhibitors is that of the partial formula

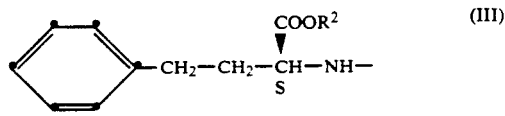

(III)

wherein $R^2$ is hydrogen or lower alkyl, that is in the S-configuration. R-2-hydroxy-4-phenylbutyric acid can be used for the preparation of ACE inhibitors in known manner and with a high degree of enantiomeric purity being achieved (see in this connection, for example, European Patent Application 206993). The particular value of the present invention is inter alia that, in the synthesis of ACE inhibitors, which comprises numerous steps, it is possible to use an enantiomerically pure compound at a relatively early stage of the synthesis. Of particular interest in this connection is the preparation of the ACE inhibitor 1-carboxymethyl-3S-[(1S-ethoxycarbonyl-3-phenylpropyl)amino]-2,3,4,5-tetrahydro-1H-benzazepin-2-one. S-2-hydroxy-4-phenylbutyric acid is suitable in analogous manner for the preparation of enantiomers of the ACE inhibitor and for toxicological studies.

The following Examples are intended to illustrate the present invention without implying any limitation thereof to the scope of the Examples.

Abbreviations ee—enantiomeric excess
FDH—formate dehydrogenase
HPLC—high pressure liquid chromatography
$K_I$—inhibition constant
$K_M$—Michaelis-Menten constant
LDH—lactate dehydrogenase
NADH—nicotinamide adenine dinucleotide
rpm—rotations per minute
U—unit of enzyme activity (under defined reaction conditions, 1 U produces a substance conversion of 1 μmol/min)
$V_{max}$—maximum reaction rate

EXAMPLE 1

Enzymatic reduction of 2-oxo-4-phenylbutyric acid with microbial crude extracts (general instructions)

The test strains are cultivated with 3 g/l D- or L-lactate for 3 days at 28° C., with stirring (250 rpm), in 200 ml of nutrient solution 148 (22 g/l glucose, 5 g/l Lab-Lemco beef extract [Oxoid], 5 g/l peptone C, 5 g/l yeast extract, 3 gl Bacto-Casein [Difco], 1.5 g/l NaCl, pH 6.5) or nutrient solution MV7 (2 g/l NH$_4$NO$_3$, 1.4 g/l Na$_2$HPO$_4$, 0.6 g/l K$_2$HPO$_4$, 0.2 g/l MgSO$_4$.7H$_2$O, 0.01 g/l CaCl$_2$.2H$_2$O, 0.001 g/l FeSO$_4$.7H$_2$O, 1 ml of trace element solution [20 mg/l Na$_2$MoO$_4$.2H$_2$O, 20 mg/l Na$_2$B$_4$O$_7$.10H$_2$O, 20 mgl ZnSO$_4$.7H$_2$O, 20 mg/l MnSO$_4$.H$_2$O, 20 mg/l CuSO$_4$.5H$_2$O], pH 6.5). The cells are washed with phosphate buffer pH 7.0 and harvested by centrifugation (20 min., 20000 rpm) in a Sorvall centrifuge, Rotor SS34. The cells are then disrupted at 4° C by ultrasound treatment at 375 W for 45 minutes in an Ultrasonics Celldisrupter W-375. After centrifuging once more, the enzyme crude extract is incubated with the substrate in the following test mixture at 28° C., with stirring, for 3 to 5 days (until conversion is complete):

5 ml centrifugation supernatant (crude extract)
20 ml phosphate buffer pH 7 (0.069 M)
3 g/l 2-oxo-4-phenylbutyric acid
18 g/l ethanol
1 g/l NAD(H)
100 U yeast alcohol dehydrogenase (Boehringer)

When the reaction is complete, the solution is adjusted to pH 2 with 2N hydrochloric acid. The product which then crystallises out is extracted with ethyl acetate. The solvent is distilled off and the residue is dried in vacuo to yield crystalline 2-hydroxy-4-phenylbutyric acid of different enantiomeric purities depending on the microbial extract tested.

The crystalline acid is dissolved in absolute ethanol and reacted with hydrogen chloride gas for 24 hours at room temperature. After distilling off the alcohol and briefly degassing under a high vacuum, a pale yellow oil remains which is analysed by HPLC at 25° C./32 bar over a chiral column (250×4.6 mm i.d., throughput 1 ml/min, stationary phase Chiralcel OD [Stehelin, Basle]Type OD-5-15-20925, mobile phase 90% hexane - 10% isopropanol - 0.1 % diethylamine). The substances to be analysed are present in the eluant in a concentration of 1 mg/ml (quantity injected 10 μl). Scanning is carried out at a wavelength of 210 nm, and evaluation by surface area comparison with an external standard. The ee values found for the microbial extracts investigated are set forth in Table 2.

TABLE 2

| test strain (extract) | ee | C-source for cultivation |
|---|---|---|
| Lactobacillus brevis DSM 20054 | 28% (R) | glucose |
| Staphylococcus epidermidis DSM 20042 | 78% (R) | glucose |
| Saccharomyces cerevisiae baker's yeast Migros 76 10 2011 | 96% (R) | glucose |
| Kloeckera sp. 2201 ATCC 48 180 (Candida boidinii, T. Egli 2201) | 97% (R) | glucose |
| Saccharomyces cerevisiae baker's yeast Migros 76 10 2011 | 90% (R) | L-lactate |

Enantiomeric excess in the reduction with microbial crude extracts

TABLE 2-continued

| test strain (extract) | ee | C-source for cultivation |
|---|---|---|
| Hansenula polymorpha CBS 4732 | 98% (R) | D-lactate |

Enantiomeric excess in the reduction with microbial crude extracts

EXAMPLE 2

Enzymatic reduction of 2-oxo-4-phenylbutyric acid with commercially available dehydrogenases The substrate is incubated with a commercially available dehydrogenase in the following test mixture at 28° C., with gentle stirring, for 3 to 7 days (until conversion is complete):

50 ml phosphate buffer pH 7 (0.069 M)
3 g/l 2-oxo-4-phenylbutyric acid
18 g/l ethanol
200 U yeast alcohol dehydrogenase (Boehringer)
200 U test enzyme (commercially available dehydrogenase)
1 g/l NAD(H)

The enantiomeric excess of R-2-hydroxy-4-phenylbutyric acid or S-2-hydroxy-4-phenylbutyric acid is determined as described in Example 1. The results are set forth in Table 3.

TABLE 3

Enantiomeric excess in the conversion of 2-oxo-4- phenylbutyric acid with commercially available dehydrogenases

| enzyme tested | ee |
|---|---|
| D-LDH from Lactobacillus leichmannii (Boehringer) | >99% (R) |
| D-LDH from Lactobacillus leichmannii (Sigma) | >98% (R) |
| D-LDH from Leuconstoc mesenteroides (Sigma) | >98% (R) |
| D-LDH from Staphylococcus epidermidis (Sigma) | ~100% (R) <0,2% (S) |
| L-LDH from bovine heart (Fluka) | ~100% (S) |

A comparison of the ee values shows that isolated enzymes are more suitable than microbial crude extracts for the stereospecific reduction of the substrate since the enatiomeric excess of R- or S-2-hydroxy-4-phenylbutyric acid for isolated enzymes is significantly higher. In order to obtain similarly high ee values, the selective enzymes would have to be enriched from the crude extracts in addition by purification steps.

EXAMPLE 3

Enzymatic reduction of 2-oxo-4-phenylbutyric acid with commercially available dehydrogenases in an enzyme membrane reactor (EMR)

The continuous conversion of 2-oxo-4-phenylbutyric acid to R- or S-2-hydroxy-4-phenylbutyric acid is carried out in a flat membrane enzyme membrane reactor (EMR) maintained at 25° C. with a reactor volume of 10 ml. The cellulose acetate ultrafiltration membrane of 62 mm diameter has a nominal exclusion limit of 10,000 daltons and has been pre-coated with 50 mg of bovine serum albumin.

The optimum reaction procedure is determined by analysis with the aid of the experimentally determined enzyme kinetics, i.e. by determining the kinetic constants ($K_M$, $K_I$, $V_{max}$) for the D- or L-lactate dehydrogenase and formate dehydrogenase for substrate concentrations of 50, 100 and 150 mM, by simulating the behaviour of the reactor by calculation of the mass balances of the reactants. The "Runge-Kutta-Program" is applied, in which the parameters dwell time, educt concentration and cofactor concentration and the half lives of the enzymes are varied (see Hoffmann & Hoffmann, "EinfüUhrung in die Optimierung mit Anwendungs-beispielen aus dem Chemie-Ingenieurwesen", Weinheim 1971).

The substrate solution contains 50 mM 2-oxo-4-phenylbutyric acid, 300 mM potassium formate and 0.1 mM NAD(H). 2.6 U/ml D-LDH and 4.8 U/ml FDH or 1.4 U/ml L-LDH and 2.5 U/ml FDH are introduced. The reaction solution is pumped into the reactor continuously at a rate of 10 ml/h and the product is drawn off through the membrane. The dwell time in the reactor is 60 minutes for the conversion with D-LDH and 120 minutes for the conversion with L-LDH. The enzyme activities are continuously monitored and, if necessary, kept constant by further addition. The production data are given in Table 4.

TABLE 4

| | Production data | |
|---|---|---|
| | D-LDH | L-LDH |
| duration of test (continuous production): | 450 h | 100 h |
| conversion: | ϕ 84% | ϕ 77% |
| enantiomeric excess: | ~100% ee (R) | ~100% ee (S) |
| product concentration: | ϕ 42.5 mM = 7.65 g/l | ϕ 38.5 mM = 6.8 g/l |
| productivity: | 184 g/l × d | 1.6 g/l × d |

EXAMPLE 4

Synthesis of 1-carboxymethyl-3S-[(1S-ethoxycarbonyl-3-phenyl-propyl)-amino]-2,3,4,5-tetrahydro-1H-benzazepin-2-one (ACE inhibitor)

4.1. Synthesis of R-2-hydroxy-4-phenylbutyric acid ethyl ester 5.0 g of R-2-hydroxy-4-phenylbutyric acid are dissolved in 50 ml of absolute ethanol and reacted with hydrogen chloride gas for 24 hours at room temperature. After distilling off the alcohol and briefly degassing under a high vacuum, a pale yellow oil (5.7 g) remains of which, according to HPLC analysis over a chiral column (see Example 1), ≧99.8% consists of the R-configured ester. Less than 0.2% consists of the S-configured ester. The oil is distilled at 100° to 105° C. and 6.5 pascals to yield 5.2 g of (−)-R-2-hydroxy-4-phenylbutyric acid ethyl ester with an optical rotation of $[\alpha]_D^{20} = -20.8°$ (1% in chloroform).

4.2. Synthesis of (+)-R-2-(4-nitrobenzenesulfonyloxy)-4- phenylbtyric acid ethyl ester 9.75 g (46.8 mmol) of (−)-R-2-hydroxy-4-phenylbutyric acid ethyl ester (≧99.6% ee) are dissolved in 50 ml of toluene, 11.4 g of 4-nitrobenzenesulfonyl chloride are added thereto and the reaction mixture is then cooled to 0° C. After the addition of 6.25 g of triethylamine, the reaction mixture is warmed to room temperature over a period of 30 minutes and worked up, affording, in quantitative yield, (+)-R-2-(4-nitrobenzenesulfonyloxy)-4-phenylbutyric acid ethyl ester having an optical rotation of $[\alpha]_D^{20} = +13.2°$ (3% in absolute ethanol).

4.3. Synthesis of 1-carboxymethyl-3S-[(1S-ethoxycarbonyl-3-phenylpropyl)-amino]-2,3,4,5-tetrahydro-1H-benzazeoin-2- one 46.1 g of 3-(S)-aminobenzazepin-2-one-1-N-acetic acid tert.-butyl ester, 84.3 g of optically pure (≧99.6 % ee) (+)-R-2-(4-nitrobenzenesulfonyloxy) -4-phenylbutyric acid ethyl ester and 19.53 g of N-methylmorpholine are reacted without solvent for 9 hours at 75° to 80° C. The N-methylmorpholine salt of 4-nitrobenzenesulfonic acid which precipitates is dissolved by the addition of 250 ml of ethyl acetate and 150 ml of water, adjusted to pH 8.8 with approximately 150 ml of 2N soda solution, and the ethyl acetate phase is separated and washed twice more with water. The ethyl acetate is distilled off to yield an oil (98 g) which in HPLC shows a ratio of the diastereoisomers of at least SS:SR=99.8:0.2.

The crude active substance is prepared by passing 54 g of hydrogen chloride gas into a solution of 96 g of the above-mentioned oil in 200 ml of ethyl acetate at 0° to 10° C. When solvolysis of the tert.-butyl ester is complete, the active substance is obtained in the form of a finely crystalline suspension. The excess hydrogen chloride is removed completely by repeatedly distilling off ethyl acetate in vacuo. The highly concentrated crystal suspension is then diluted with 200 ml of acetone, filtered off at 15° C. and washed twice with 50 ml of ethyl acetate each time. After drying in vacuo at 60° C. until constant weight is achieved, 62.5 g (85.4%) of a virtually white active substance having a ratio of the diastereoisomers of SS:SR=99.9:0.1 are isolated; $[\alpha]_D^{20} = -138°$ (1% in absolute ethanol), m.p. 181° C.

EXAMPLE 5

Synthesis of 1-carboxymethyl-3S-[(1R-ethoxycarbonyl-3-phenyl-propyl)-amino]-2,3,4,5-tetrahydro-1H-benzazepin-2-one 1-Carboxymethyl-3S-[(1R-ethoxycarbonyl-3-phenylpropyl)-amino]-2,3,4,5-tetrahydro-1H-benzazepin-2-one is prepared from S-2-hydroxy-4-phenylbutyric acid in a manner analogous to that described in Example 4.

What is claimed is:
1. A process for the preparation of the R-enantiomer of 2-hydroxy-4-phenylbutyric acid of the formula

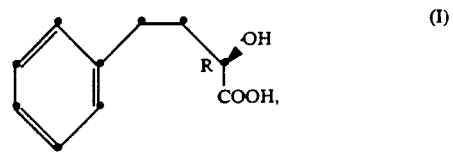

(I)

or the S-enantiomer of 2-hydroxy-4-phenylbutyric acid of the formula

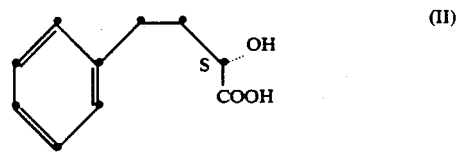

(II)

which process comprises reducing 2-oxo-4-phenylbutyric acid with the enzyme D-lactate dehydrogenase (D-LDH) from Staphylococcus epidermidis or with the enzyme L-lactate dehydrogenase (L-LDH) from bovine heart, respectively, in the presence of an electron donor and an enzyme/substrate system for regenerating the electron donor.

2. A process according to claim 1 for the preparation of R-2-hydroxy-4-phenylbutyric acid, which comprises reducing 2-oxo-4-phenylbutyric acid with the enzyme D-lactate dehydrogenase (D-LDH) from *Staphylococcus epidermidis* in the presence of an electron donor and an enzyme/substrate system for regenerating the electron donor.

3. A process according to claim 1 which comprises preparing 2-hydroxy-4-phenylbutyric acid in an enantiomeric purity of more than 99.6% ee (enantiomeric excess).

4. A process according to claim 1 which comprises using nicotinamide adenine dinucleotide (NAD(H)) as the electron donor and formate dehydrogenase (FDH)/formate as the enzyme/substrate system for regenerating the electron donor.

5. A process according to claim 1 which comprises using nicotinamide adenine dinucleotide (NAD(H)) as the electron donor and alcohol dehydrogenase (ADH)/ethanol as the enzyme/substrate system for regenerating the electron donor.

6. A process according to claim 1 which comprises carrying out the enzymatic conversion continuously.

7. A process according to claim 1 which comprises carrying out the enzymatic conversion in an enzyme membrane reactor.

8. A process according to claim 7, which comprises carrying out the enzymatic conversion in an enzyme membrane reactor
   a) that is equipped with an ultrafiltration membrane,
   b) that contains a reaction mixture consisting of a solution of a formate dehydrogenase or an alcohol dehydrogenase, the D-lactate dehydrogenase from *Staphylococcus epidermidis* or the L-lactate dehydrogenase from bovine heart, and nicotinamide adenine dinucleotide (NAD(H)),
   c) to which there is continuously fed an aqueous solution of the substrate 2-oxo-4-phenylbutyric acid and formate or ethanol, respectively and
   d) in which the compound formed is continuously drawn off downstream of the membrane.

9. A process according to claim 7 which comprises carrying out the enzymatic conversion in an enzyme membrane reactor
   a) that is equipped with an ultrafiltration membrane having a nominal exclusion limit of from 5,000 to 100,000 daltons,
   b) that contains a reaction mixture consisting of a solution of a formate dehydrogenase or an alcohol dehydrogenase, the D-lactate dehydrogenase from *Staphylococcus epidermidis* or the L-lactate dehydrogenase from bovine heart, and from 0.01 to 1 mM of nicotinamide adenine dinucleotide (NAD(H)),
   c) to which there is continuously fed an aqueous solution of up to 500 mM of the substrate 2-oxo-4-phenylbutyric acid, and from 100 to 1200 mM of formate or ethanol, respectively, and
   d) in which the compound formed is continuously drawn off downstream of the membrane.

10. A process according to claim 7 which comprises carrying out the enzymatic conversion in an enzyme membrane reactor of which the ultrafiltration membrane has been pre-coated with a non-specific protein.

* * * * *